United States Patent [19]

Ogirala

[11] Patent Number: 5,301,684
[45] Date of Patent: Apr. 12, 1994

[54] BIOPSY NEEDLE

[75] Inventor: Raja G. Ogirala, Mount Kisco, N.Y.

[73] Assignee: International Electronic Technology Corp., Farmingdale, N.Y.

[21] Appl. No.: 53,986

[22] Filed: Apr. 27, 1993

[51] Int. Cl.$^5$ .............................................. A61B 10/00
[52] U.S. Cl. ...................................... 128/754; 606/170
[58] Field of Search ............................... 128/751–754; 606/167, 170

[56] References Cited

U.S. PATENT DOCUMENTS

| | | | |
|---|---|---|---|
| 4,517,965 | 5/1985 | Ellison | 128/754 |
| 5,112,346 | 5/1992 | Hiltebrandt et al. | 606/170 |

FOREIGN PATENT DOCUMENTS

| | | | |
|---|---|---|---|
| 3007165 | 9/1981 | Fed. Rep. of Germany | 128/751 |
| 2161707 | 1/1986 | United Kingdom | 606/170 |

Primary Examiner—Max Hindenburg
Attorney, Agent, or Firm—Sprung Horn Kramer & Woods

[57] ABSTRACT

A biopsy needle for removal of tissue from human or animal bodies incorporates a tubular elongated body (1) and a plunger (7) arranged both slidably and rotatably within the body. The plunger is pointed at one end and has a tissue-removing edge directed backwardly from the pointed end and formed on a flap (9) supported by the body (1) and movable between a retracted position in which the tissue-removing edge lies within the lateral confines of the body (1) and an extended position in which the tissue-removing edge lies beyond the lateral confines of the body (1). The wall of the body (1) is formed with an aperture (2) with which the flap may be brought into register by movement of the plunger (7). A pin and slot arrangement serves to selectively engage the plunger (7) and body (1) together while permitting limited rotational and translational movement of the plunger in prescribed directions with respect to the body, the improvement comprising a mechanical spring interposed between the plunger and body for applying a biasing force to the engaging means, thereby to maintain the plunger and body in their relative positions. The needle is used by inserting it into the tissue, extending the flap to entrain a portion of tissue, retracting the flap and withdrawing the plunger from the body, bringing with it the portion of tissue.

10 Claims, 2 Drawing Sheets

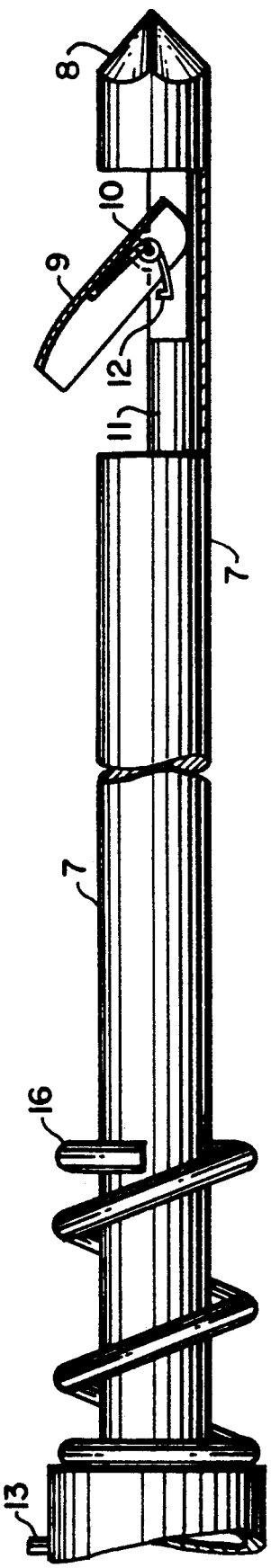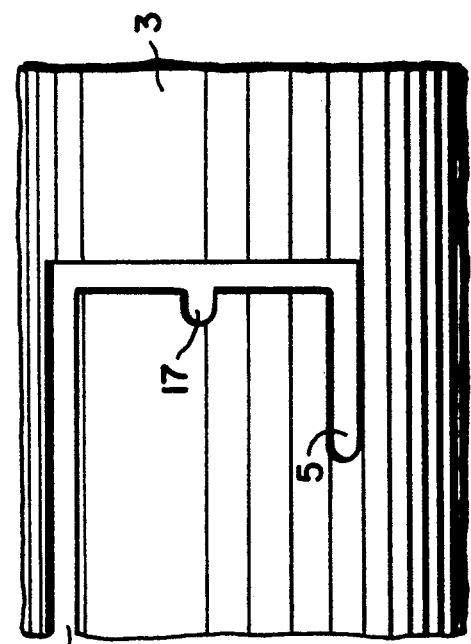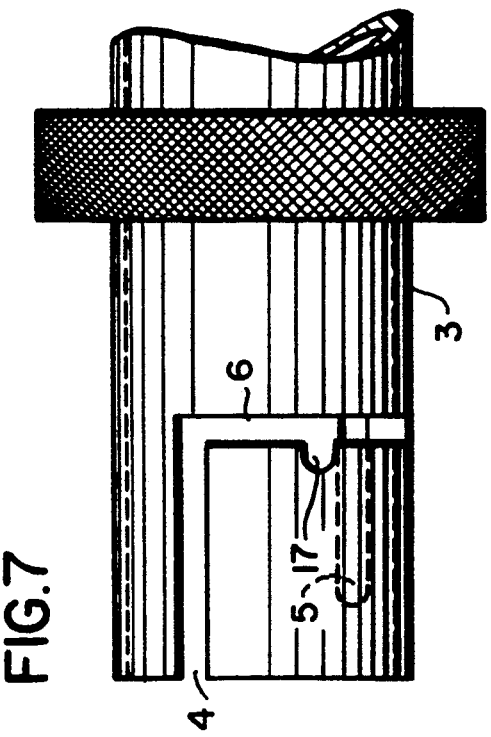

BIOPSY NEEDLE

BACKGROUND OF THE INVENTION

The subject of this invention is a needle for performing biopsies, i.e. for removal of pieces of tissue from human or animal bodies. The needle which is the subject of this application is of particular use in performing pleural biopsies.

Needles for performing biopsies are well known and normally comprise a probe which carries near the distal end a scoop projecting from the side of the probe, a biopsy being performed by inserting the probe through an incision made in the skin and pressing the probe into the body far enough for the scoop to reach the position of the body from which a portion is to be removed. The probe is then withdrawn, the scoop entraining a portion of the tissue of the body, and as the probe is removed this portion of tissue held by the scoop is brought back out for medical examination. Such known biopsy needles suffer from the disadvantage that their results are extremely unpredictable and in fact usually a suitable portion of tissue is removed in little more than 70% of such biopsy operations. Even when a satisfactory portion of tissue is removed, this frequently is accompanied by a piece of unwanted tissue Also, the probe may cause more damage than necessary to surrounding tissue and if the tissue sample obtained is unsatisfactory, the needle must be re-inserted into the body and a fresh attempt made to obtain a satisfactory tissue sample.

The International Patent Publication No. WO 89/05608 discloses a biopsy needle which gives a high degree of success in removing satisfactory samples at a first attempt, a success rate normally well above 90%, and which readily removes cleanly a sample of wanted tissue without dragging with it portions of unwanted tissue.

A biopsy needle according to this disclosure incorporates an elongated body pointed at one end having a tissue-removing edge directed backwardly from the pointed end. The tissue-removing edge is formed on a flap supported by the body and is movable between a retracted position, in which the tissue-removing edge lies within the lateral confines of the body, and an extended position in which the tissue-removing edge lies beyond the lateral confines of the body.

The proximal end of the needle, i.e., the end remote from the pointed end, is formed as a handle supporting operating means coupled to the flap and operative to move the flap from the retracted position to the extended position and vice versa.

The operating means includes a means to lock the flap in the chosen position.

The flap may be formed as a flat flap or may be curved in the form of a scoop.

The tissue-removing edge may be formed as a straight edge or may be formed with serrations.

The flap is mounted on a plunger slidable within the tubular body. The wall of the tubular body in this construction is formed with an aperture with which the flap may be brought into register by an appropriate sliding movement of the plunger.

The flap is pivoted at one end to the plunger and is spring-urged to swing outwardly from the plunger, the tissue-removing edge being at the end of the flap remote from the pivot. In an alternative construction the flap may be formed of spring material, is formed at one end with the tissue-removing edge and is attached at the other end to the plunger, the flap being shaped to tend to spring outwardly from the plunger.

The interior of the tubular body preferably has a circular cross section so that the plunger is rotatable as well as slidable in the tubular body.

The handle is tubular and may thereupon be formed with a slot having two axially disposed portions circumferentially spaced and connected at their distal ends by a circumferential portion, one of the axially disposed slot portions being open at its proximal end. The plunger presents a pin engaging the slot, the position of the pin on the plunger and the positions of the various portions of the slot with respect to the tubular body being such that when the pin on the plunger is engaged with the open ended axial portion of the slot the flap is circumferentially displaced from the aperture in the tubular body. The length of this axial portion is such that, when the pin is at the distal end of the slot, the flap is nearer the distal end of the tubular body than the aperture while being still circumferentially displaced from the aperture. Rotating the plunger so that the pin moves along the circumferential portion of the slot to the end where it joins the axial portion of the slot brings the flap into line with the aperture although the flap is still nearer the distal end of the tubular body than the aperture. Then retracting the plunger along this other axial portion of the slot towards the proximal end of the slot brings the flap into register with the aperture in the tubular body and frees the flap to swing out and project through the aperture.

This biopsy needle, while constituting a significant improvement over prior known biopsy needles, has been found to present the drawback that the plunger, which fits loosely within the tubular body, can easily rotate and slidably translate within tube, and can therefore change the relative positions of the flap and aperture or even accidentally become disengaged from the tubular body.

SUMMARY OF THE INVENTION

It is a principal object of the present invention, therefore, to provide a biopsy needle of the type disclosed in the International Patent Publication No. WO 89/05608 which does not exhibit the disadvantages referred to above.

This object, as well as further objects which will become apparent from the discussion that follows, are achieved, in accordance with the present invention, by providing a spring, such as a helical compression spring, between the plunger and the tubular body, so as to present a spring tension between these two elements tending to maintain their relative positions.

Advantageously, the slot on the tubular body which engages the locating pin on the plunger includes a notch at approximately the center portion thereof. This notch in the slot serves as a detent for the plunger and pin to hold the same in position.

For a full understanding of the present invention, reference should now be made to the following detailed description of the preferred embodiments of the invention as illustrated in the accompanying drawings.

BRIEF DESCRIPTION OF THE DRAWINGS

FIG. 6 is an enlarged view of both the proximal and distal ends of the plunger showing the helical spring according to the present invention.

FIG. 7 is an enlarged view of the proximal end of the tubular body showing a notch which serves as a detent.

FIG. 8 is a representative diagram illustrating the entire slot on the handle of the tubular body.

DESCRIPTION OF THE PREFERRED EMBODIMENTS

Figure 5:
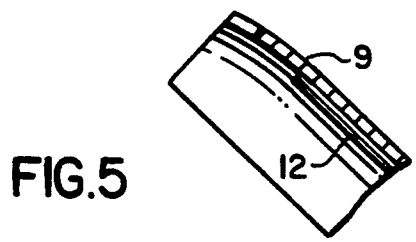
FIG. 5 is an enlarged view of the flap at the distal end of the plunger.

In the drawings 1 denotes a tubular body formed with a slot 2 in the wall near the distal end of the body 1 and 3 denotes a handle attached to the tube 1, the handle 3 being formed with a slot having two axial portions 4 and 5 joined at the distal ends of the slots by a circumferential portion 6. A plunger 7, slidable through the tubular body portion 1, is pointed as at 8 at the distal end and carries a flap 9 pivoted at 10 to the plunger 7. The flap 9 is accommodated in a recess 11 in the plunger 7 large enough to hold the flap 9 within the diametral confines of the plunger 7 when the flap is folded downwardly towards the plunger 7. The flap is normally urged by a spring 12 (FIG. 6) to move to the extended position as illustrated. The top tissue-removing edge of the flap is preferably formed with serrations (FIG. 5). The plunger presents a pin 13 engageable with the slot constituted by the portions 4, 5 and 6 in the handle of the body portion 1. The arrangement of the pin 13 and of the slot 4, 5, 6 (FIGS. 7 and 8) is such that, when the plunger 7 is inserted into the body portion 1 and moved towards the distal end of the body portion 1, in the initial act of entering the plunger 7 into the body portion 1 the flap is forced to move into the recess 11 as the distal end of the plunger 7 moves through the body portion 1 towards the distal end of the body portion 1. The plunger 7 is moved to cause the pin 13 to enter the slot portion 4. In this orientation of the plunger 7 the flap 9 is out of line with the slot 2 in the body portion 1, i.e., it is displaced circumferentially from the slot 2. As the plunger 7 is advanced to the position where the pin 13 comes against the distal end of the slot portion 4 adjacent the slot portion 6 the plunger is now in a position in which the flap 9 is nearer the distal end of the body portion 1 than the slot 2 but is still retained in its retracted position by the wall of the tubular body portion 1. The plunger 7 is now rotated to cause the pin 13 to move along the circumferential slot 6 until it is opposite the slot portion 5. In this position the flap 9 is in line with the slot 2 in the body portion 1 although still nearer the distal end of the body portion 1 than the slot 2 and still retained in its retracted position. Withdrawal of the plunger 7 causing the pin to move along the slot portion 5 causes the flap 9 to move back from the distal end of the body portion 1 until it now registers with the slot 2 in the body portion 1 whereupon the spring 12 causes the flap 9 to extend out through the slot 2.

Figure 1:
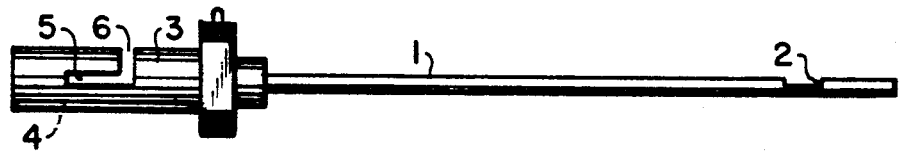
FIG. 1 illustrates a tubular body portion of the biopsy needle according to the invention.
Figure 2:
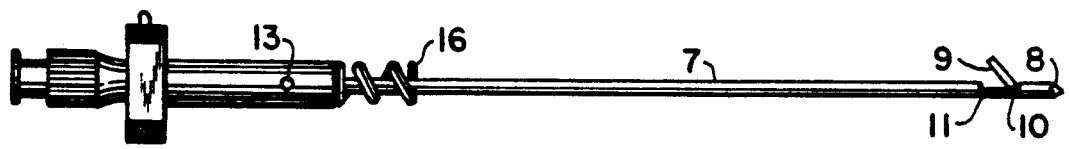
FIG. 2 illustrates a plunger movable through the tubular body portion.
Figure 3:
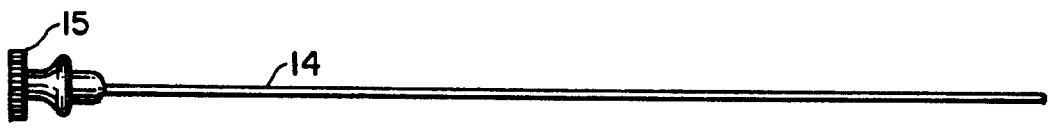
FIG. 3 illustrates an obturator needle, movable through the plunger.
Figure 4:
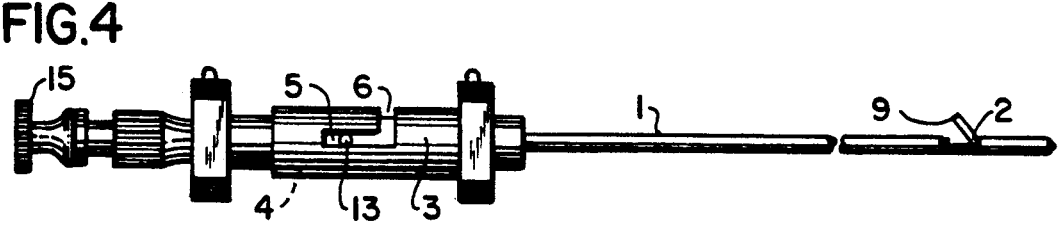
FIG. 4 illustrates an assembled biopsy needle according to the invention with the flap in the extended position.

An obturator needle (FIG. 3), movable through a central opening within the plunger, serves, when inserted to its fullest extent, to press any portion of a sample which has entered the plunger out through the opening at the flap. The obturator needle is comprised of a needle portion 14 and a knurled knob 15 at one end.

As indicated in detail in FIG. 6, the plunger 7 is provided with a helical spring 16 to create spring tension when the plunger is inserted into the tubular body to such depth that the pin 13 is engaged with the slot 4, 5 and 6. This spring tension prevents the plunger from accidentally rotating or sliding within the tubular body when the pin 13 is engaged with the slot portions 6 and 5, and particular when the pin is engaged in a notch 17 that serves as a detent.

In performing a biopsy the needle, with the flap 9 out of register with the slot 2, is entered into the organ from which a tissue sample is to be taken through an incision made in the skin. When the distal end is at the position in the body where a sample is to be taken the movements described above to cause the flap 9 to protrude from the body portion I are performed. Thereupon the needle is withdrawn for a short distance to cause the flap 9 to remove and entrain a portion of the tissue of the organ. The plunger 7 is now advanced again towards the distal end of the body portion. The pin 13 is moved along the slot portion 5 up to the circumferential slot 6 and rotated until it reaches the detent. This again causes the flap 9 to come against the forward end of the slot 2 and to retract and enter the recess 11, taking with it the portion of tissue removed. The plunger is then rotated so that the pin 13 moves along the circumferential slot 6 until it is opposite the slot portion 5. This again brings the retracted flap 9 out of alignment with the slot 2 in the body portion 1. The plunger 7 may then be withdrawn completely from the body portion 1, the pin 12 moving along and out of the slot portion 5. Complete removal of the plunger 7 brings with it the portion of tissue removed by the flap 9 leaving the body portion 1 still projecting into the organ. The sample removed by the flap 9 may now be examined. If it is satisfactory the body portion 1 may be removed from the body without further damage to the body. If the portion of tissue removed is not satisfactory, the plunger 7 may be reinserted as before and a fresh sample taken. It may be desired to take several samples at different depths in the body. This can be done merely by pressing the needle different distances into the body. All this may be done as an operation with only one insertion of the needle so that the minimum of damage is done to the organ and at the same time the samples removed can be seen to be completely satisfactory for clinical purposes before the needle is removed.

There has thus been shown and described a novel biopsy needle which fulfills all the objects and advantages sought therefor. Many changes, modifications, variations and other uses and applications of the subject invention will, however, become apparent to those skilled in the art after considering this specification and the accompanying drawings which disclose the preferred embodiments thereof. All such changes, modifications, variations and other uses and applications which do not depart from the spirit and scope of the invention are deemed to be covered by the invention, which is to be limited only by the claims which follow.

What is claimed is:

1. In a biopsy needle comprising (1) a tubular elongated body, (2) a plunger, slidably and rotatably arranged within the body, said plunger being pointed at one end and having a tissue-removing edge directed backwardly from the pointed end and (3) means for selectively engaging the plunger and body together while permitting limited rotational and translational movement of the plunger in prescribed directions with respect to the body, the improvement comprising a mechanical spring interposed between the plunger and body for applying a biasing force to the engaging means, thereby to maintain the plunger and body in their relative positions.

2. A biopsy needle according to claim 1, wherein the tissue-removing edge is formed on a flap supported by the body and movable between a retracted position in which the tissue-removing edge lies within the lateral confines of the body and an extended position in which the tissue-removing edge lies beyond the lateral confines of the body.

3. A biopsy needle according to claim 2, wherein the flap is curved in the form of a scoop.

4. A biopsy needle according to claim 2, wherein the proximal end of the needle, remote from the pointed end, is formed as a handle supporting operating means coupled to the flap for moving the flap from the retracted position to the extended position and vice versa.

5. A biopsy needle according to claim 4, wherein the handle is tubular; wherein the engaging means includes a slot in the handle having two axially disposed portions circumferentially spaced and connected at their distal ends by a circumferential portion, one of the axially disposed slot portions being open at its proximal end; and wherein the plunger includes a pin which engages the slot, the position of the pin on the plunger and the positions of the various portions of the slot with respect to the tubular body being such that when the pin on the plunger is engaged with the open ended axial portion of the slot the flap is circumferentially displaced from the aperture in the tubular body and when the pin is engaged with the other axial portion of the slot the flap is in line with the aperture in the tubular body and is movable into register with the aperture.

6. A biopsy needle according to claim 5, wherein a notch is provided in the circumferential portion of the slot to serve as a detent for the pin.

7. A biopsy needle according to claim 2, wherein the wall of the body is formed with an aperture with which the flap may be brought into register by an appropriate sliding movement of the plunger.

8. A biopsy needle according to claim 7, wherein the flap is spring-urged to swing outwardly from the plunger, the tissue-removing edge being at the end of the flap remote from the pivot.

9. A biopsy needle according to claim 7, wherein the flap is made of spring material, is formed at one end with the tissue-removing edge and is attached at the other end to the plunger, the flap being shaped to tend to spring outwardly from the plunger.

10. A biopsy needle according to claim 1, wherein the tissue-removing edge is formed with serrations.

* * * * *